United States Patent
Duflot et al.

(12) 
(10) Patent No.: US 6,274,355 B1
(45) Date of Patent: Aug. 14, 2001

(54) IMMOBILIZED MALTOGENIC α-AMYLASE AND ITS USE IN THE MANUFACTURE OF A MALTOSE-RICH SYRUP

(75) Inventors: Pierrick Duflot, Lacouture; Catherine Fouache, Sailly Labourse, both of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/473,460

(22) Filed: Dec. 28, 1999

(30) Foreign Application Priority Data

Dec. 29, 1998 (FR) .................................................. 98 16537

(51) Int. Cl.⁷ ............................. C12P 19/14; C12P 19/12; C12N 9/00; C12N 9/24
(52) U.S. Cl. ............................. 435/99; 435/100; 435/183; 435/200
(58) Field of Search ............................. 435/99, 100, 183, 435/124, 200, 158

(56) References Cited

U.S. PATENT DOCUMENTS

| | | |
|---|---|---|
| 3,708,396 | 1/1973 | Mitsuhashi et al. . |
| 4,116,771 | 9/1978 | Amots et al. . |
| 4,294,623 | 10/1981 | Hidaka et al. . |
| 4,338,398 * | 7/1982 | Yoneyama et al. ..................... 435/95 |
| 4,487,198 | 12/1984 | Miyake et al. . |
| 5,141,859 | 8/1992 | Niimi et al. . |
| 5,391,299 * | 2/1995 | Masuda et al. ........................ 210/659 |
| 5,462,864 * | 10/1995 | Niimi et al. .......................... 435/100 |

FOREIGN PATENT DOCUMENTS

| | | |
|---|---|---|
| 0 112 147 | 6/1984 | (EP) . |
| 0 860 500 | 8/1998 | (EP) . |
| 1 283 571 | 7/1968 | (GB) . |

OTHER PUBLICATIONS

Hodge, Cereal Chemistry, 01/48, pp 19–30.
Wolfrom, Methods in Carbohydrate Chemistry, 1962, pp334–335.

* cited by examiner

*Primary Examiner*—Rebecca E. Prouty
*Assistant Examiner*—Manjunath N. Rao
(74) *Attorney, Agent, or Firm*—Henderson & Sturm LLP

(57) ABSTRACT

The invention concerns an immobilized maltogenic α-amylase, which is adsorbed on particles of at least one porous substrate selected from the group consisting of phenolic resins, acrylic resins and polystyrene resins. The present invention also relates to the use of such an α-amylase for the preparation of a maltose-rich syrup.

11 Claims, No Drawings

IMMOBILIZED MALTOGENIC α-AMYLASE AND ITS USE IN THE MANUFACTURE OF A MALTOSE-RICH SYRUP

CROSS-REFERENCE TO RELATED APPLICATIONS

[Not Applicable.]

STATEMENT REGARDING FEDERALLY SPONSORED RESEARCH OR DEVELOPMENT

[Not Applicable.]

BACKGROUND OF THE INVENTION

1. Field of the Invention

The invention relates to an immobilised maltogenic α-amylase and the method of manufacturing same. It relates further to a method of manufacturing a syrup which is rich in maltose. It relates also to a method of manufacturing a syrup which is rich in maltitol from a maltose-rich syrup obtained by the method according to the present invention. It relates equally to a method of manufacturing maltitol crystallised from a maltose-rich syrup obtained by the method according to the present invention.

2. Description of the Prior Art

Methods allowing the production of maltose-rich syrups are already known. Amongst these methods it is possible to quote in particular the one described by HODGE and Coll. in "Cereal Chemistry" No. 25, pages 19–30, January 1948, and which contains a stage of precipitation of the dextrin limits by alcohol solutions, and the one described by WOLFROM and THOMPSON in "Methods in carbohydrate chemistry", 1962, pages 334–335.

Other methods of manufacturing maltose-rich syrups have also been proposed comprising a stage of adsorption on charcoal of the dextrins (U.S. Pat. No. 4,194,623), a stage of chromatography on zeolites or cationic or anionic resins (FR-A-2.510.581), a stage of ultrafiltration of maltose syrups (U.S. Pat. No. 4,429,122), the combined use of several different enzymes, that is to say an α-amylase, a β-amylase and an isoamylase or a pullulanase (FR-A-2.012.831).

This last technique presents, in relation to the preceding ones, numerous advantages. It suffers nevertheless from certain disadvantages, including in particular the one residing in the fact that the saccharifications have to be carried out with very low contents of dry matter, of the order of 20 g/l, in order to obtain a maximum hydrolysis efficiency of the enzymes.

The document FR-A-2.000.580 describes a method of preparing a syrup with a high content of maltitol by hydrogenation of a syrup with a high content of maltose which is obtained by liquefaction of a starch milk with a low content of dry matter to a dextrose equivalent lower than 2, the product thus obtained being saccharified under the action of specific enzymes.

This process is expensive, gives a mediocre yield and gives rise to problems of bacterial contamination and to occurrences of retrogradation of the amylose. In addition, the syrup obtained contains proportions of polymers with a degree of polymerisation (DP in the rest of the specification) greater than or equal to 4, which are a nuisance.

More recently, the document U.S. Pat. No. 5,141,859 proposed a method of manufacturing a syrup with a high maltose content, using two successive stages of saccharification. This document advocates in fact a method comprising a first stage of saccharification in the presence of a β-amylase and a subsequent stage of saccharification in the presence of a maltogenic α-amylase. According to this document, the maltogenic α-amylase is used, after the first stage of saccharification with the β-amylase, to hydrolyse the oligosaccharides (from DP3 to DP7) and essentially the maltotriose (trisaccharide) into maltose and glucose.

In a surprising and unexpected manner, the Applicant has noted that syrups with a maltose content as high as those described in the document U.S. Pat. No. 5,141,859 could be obtained by saccharifying a starch milk liquefied by means of an immobilised maltogenic α-amylase.

To the knowledge of the Applicant only document FR-A-2.356.665 has proposed immobilising an α-amylase termed maltogenic, but on a very specific substrate constituted by casein granules essentially covered with a proteinic layer permeable to the liquids in which the enzyme is cross-linked in common with egg albumin by glutaric aldehyde. Furthermore, according to this document, the use (of which no example was given) of maltogenic α-amylase immobilised on a porous substrate for processing a starch hydrolysate proves theoretically impossible for reasons of steric inhibition, the diffusion of the oligosaccharides of DP6 to DP10 contained in such a hydrolysate towards the enzyme enclosed within the porous structure being inhibited in view of the size of the molecules.

Against all expectation and contrary to the teaching of the document FR-A-2.356.665, the Applicant has highlighted on the one hand that it was possible to immobilise a maltogenic α-amylase on a porous substrate, and, on the other hand, that such a maltogenic α-amylase was capable of hydrolysing oligosaccharides of DP3 to DP7.

DETAILED DESCRIPTION OF THE INVENTION

The invention proposes, therefore, an immobilised maltogenic α-amylase, characterised by the fact that it is adsorbed on particles of at least one porous substrate. Advantageously, such a porous substrate is selected from the group made up of phenolic resins, acrylic resins and polystyrene resins.

The invention also proposes a method of immobilising a maltogenic α-amylase according to the invention, characterised by the fact that it comprises the stages consisting of:

(a) putting a maltogenic α-amylase into solution;

(b) putting particles of at least one porous substrate into suspension;

(c) bringing said solution into contact with said suspension at ambient temperature with a view to obtaining an immobilised maltogenic α-amylase.

The invention also proposes a method of manufacturing a maltose-rich syrup, comprising the successive stages consisting of:

(a) carrying out liquefaction of a starch milk;

(b) carrying out saccharification of the liquefied starch milk in the presence of a β-amylase and at least one debranching enzyme chosen from the group made up of pullulanases and isoamylases;

(c) carrying out molecular sieving of the liquefied and saccharified starch milk so as to collect a fraction enriched with maltose and a fraction depleted of maltose;

(d) bringing said fraction enriched with maltose into contact with an immobilised maltogenic α-amylase according to the invention with a view to obtaining a syrup which is rich in maltose.

Thus the invention relates firstly to an immobilised maltogenic α-amylase. In the sense of the present invention, what is meant by "α-amylase" is an α-amylase capable of hydrolysing oligosaccharides (from DP3 to DP7) and essentially maltotriose (trisaccharide), into maltose and glucose. According to the present invention, maltogenic α-amylase is advantageously one of those marketed by the company NOVO, under the names Maltogénase® 4000 L and NOVAMYL®.

The Applicant recommends, however, proceeding to a purification of the commercial maltogenic α-amylase, before carrying out the immobilisation of same.

It has indeed been noted that the commercial enzymatic preparations could be contaminated by parasitic enzymatic activities, such as protease or glucosidase activities.

This supplementary purification makes it possible, moreover, to increase the specific activity of the maltogenic α-amylase thus prepared, which increases accordingly the potential for converting the maltotriose by the enzyme in its immobilised form. The purification of the commercial maltogenic α-amylase can be carried out by any means known by the person skilled in the art.

Advantageously, this purification can be carried out by the succession of stages consisting in dialysing the commercial preparation (using, for example, a dialysis membrane supplied by DISLAB, with the trade name ROTH®, cut-off threshold between 10 and 20,000 dalton), precipitating the commercial solution thus dialysed with 50% ammonium sulphate, processing said solution enriched with maltogenic α-amylase by gel filtration, dialysing (using a membrane of the same type as the one mentioned above) then subjecting it to processing by ion-exchange chromatography of the type CM-Sephadex C-50. It is then possible to increase the specific activity of the said enzyme between 7 and 10 times.

The immobilised enzyme according to the present invention is presented in the form of particles of at least one porous substrate chosen from phenolic, acrylic or polystyrene resins and, by preference, phenolic resins, on which substrate the enzyme is adsorbed.

According to a preferred embodiment of the invention, the particles of the substrate have an average pore diameter of between 200 and 800 Å and, preferably between 200 and 650 Å. They have, moreover, a particle diameter of between 0.2 and 1.2 mm and, preferably, between 0.5 and 0.8 mm.

Advantageously the substrate used in the present invention is for example the resin XAD761 marketed by the company ROHM & HAAS.

In order to prepare the immobilised maltogenic α-amylase according to the invention, the method described above or an equivalent method is used. After putting a purified or non-purified maltogenic α-amylase into solution and putting particles of the porous substrate into suspension, said solution is brought into contact with said suspension for at least 15 min and preferably at least 1 hour at a temperature of between 15 and 80° C.

This bringing into contact can be carried out at ambient temperature, in a continuous manner (with recycling of the enzyme solution, for example) or in a discontinuous manner.

Advantageously the maltogenic α-amylase and the particles of the porous substrate can be brought into contact at a temperature of between 20 and 70° C., preferably between 40 and 65° C. The Applicant noted in fact that the kinetics of fixing the maltogenic α-amylase on said particles were more rapid, and the quantity of enzymes fixed more significant, the increased temperature favouring hydrophobic interactions between the enzyme and its substrate.

The maltogenic α-amylase thus immobilised according to the present invention shows excellent results for the manufacture of maltose-rich syrups For this reason, the present invention also relates to a method of manufacturing a maltose-rich syrup using the maltogenic α-amylase according to the invention.

The first stage of the method according to the invention is known per se. It consists in liquefying a starch milk, the botanical origin of which can be any at all: it can come from wheat, maize or potato, for example.

This starch milk or potato flour milk has acid added to it in the case of a liquefaction termed acid, or has α-amylase added to it in the case of an enzymatic liquefaction.

In the method according to the invention, it is preferred that careful hydrolysis of the starch milk is carried out in such a way as to obtain a liquefied starch milk with a low transformation rate. Thus, the conditions of temperature, of pH, of levels of enzyme and of calcium, known to the person skilled in the art, are determined in a manner such that they make it possible to obtain a DE (Dextrose Equivalent) lower than 10, preferably lower than 6 and more particularly lower than 4. By preference, the liquefaction stage is carried out in two sub-stages, the first consisting in heating up the starch milk, for several minutes and at a temperature of between 105 and 108° C., in the presence of an α-amylase (type: TERMAMYL® 120L marketed by the firm NOVO) and a calcium-based activator, the second consisting in heating the starch milk thus treated to a temperature of between 95 and 100° C. for one to two hours.

Once the liquefaction stage is completed, in the conditions of content of dry matter, of pH, of enzyme and calcium levels well known to the expert, the next step is the inhibition of the α-amylase. This inhibition of the α-amylase can preferably be done by means of heat, by proceeding, after the liquefaction, to a thermal shock lasting several seconds at a temperature greater than or equal to 130° C.

Then the liquefied starch milk is saccharified by means of a β-amylase such as that marketed by the company GENENCOR under the designation SPEZYME® BBA 1500.

During this stage, it is advisable to associate with the β-amylase an enzyme which specifically hydrolyses the α-1,6 bonds of the starch. This addition of a debranching enzyme makes it possible on the one hand to accelerate the hydrolysis reactions without simultaneously accelerating the reversion reactions and, on the other hand, to reduce the quantity of highly branched oligosaccharides generally resisting the action of the maltogenic enzymes.

According to the invention, the debranching enzyme is selected from the group consisting of pullulanases and isoamylases. The pullulanase is, for example, the one marketed by the company ABM under the designation PULLUZYME® 750L. The isoamylase is, for example, the one marketed by the company HAYASHIBARA.

Advantageously, the method according to the invention is implemented in the presence of isoamylase, about which the Applicant noted that it made it possible to obtain a maltose syrup presenting a higher maltose content than by using a pullulanase.

In a particular embodiment of the invention, the saccharification stage can also be carried out totally or partially in the presence of fungic α-amylase by using SPEZYME® DBA 1500 (marketed by the company GENENCOR) instead of and in the place of SPEZYME® BBA 1500 (marketed by the same company).

At the end of saccharification, it is possible to add a little α-amylase and this generally improves the subsequent filtration stages. The quantities and the conditions of action of the different enzymes used in the stages of liquefaction and saccharification of the starch milk are generally those which are recommended for the hydrolysis of starch and are well known to the person skilled in the art.

Saccharification with the β-amylase associated with the debranching enzyme is carried out until the maltose hydrolysate contains at least 75% by weight of maltose and, by preference, about 80% by weight of maltose. It lasts at least 24 hours.

The hydrolysate thus saccharified is then filtered on a precoat filter or by microfiltration on membranes, then demineralised and concentrated.

At this stage of the method according to the invention, two variants can be implemented. According to a first variant, saccharification proceeds by bringing the liquefied and saccharified starch milk into contact with an immobilised maltogenic α-amylase according to the invention. This contact can be effected, for example, by passing liquefied and saccharified starch milk over columns, beds or other enclosures filled with maltogenic α-amylase according to the invention. The rate of passing is to be adapted, depending not just on the content of trisaccharides (for example between 5 and 15 bv/h (bed volumes/hours) for contents of 13 to 5%) but also on the dry matter (at 10% trisaccharides, between 6 and 4 bv/h for dry matters of 20 to 30%). At the end of this stage, it is then perhaps possible to carry out molecular sieving on the syrup thus obtained making it possible to enrich it with maltose.

According to a second variant of the method according to the invention, molecular sieving of the liquefied and saccharified starch milk is first carried out so as to collect a fraction enriched in maltose and a fraction depleted of maltose. Following this, the fraction enriched with maltose is brought into contact with a maltogenic α-amylase according to the invention, such as has been described above.

The stage of molecular sieving implemented in one or other of the two variants of the method according to the invention can consist, for example, in a stage of chromatographic separation or in a stage of separation on membranes.

The stage of chromatographic fractionation is carried out in a manner which is itself known, either discontinuously or continuously (simulated moving bed), on adsorbents such as cationic resins, or on very strongly acid zeolites, preferably charged with the aid of alkaline ions or alkaline earth ions such as calcium or magnesium, but more preferably with the aid of sodium ions.

Instead of and in the place of the stage of chromatographic separation, it is possible, in the method according to the invention, to use a stage of separation by nanofiltration on membranes. Membranes with different pore diameters are manufactured from numerous polymers and copolymers such as polysulfones, polyamides, polyacrylonitrates, polycarbonates, polyfurans etc.

Examples of the use of such membranes are described in particular in the documents U.S. Pat. No. 4,511,654, U.S. Pat. No. 4,429,122 and WO-A-95/10627.

Thanks to the method according to the invention which profits from the benefits obtained by the hydrolysis stages using the maltogenic α-amylase according to the invention, it is possible to obtain, with yields greater than 90%, a starch hydrolysate of which the maltose content is greater than 95%, and even greater than 98% when an isoamylase is used in the hydrolysis stages.

At this stage of the method according to the invention, it is perhaps possible to carry out on the hydrolysate (or maltose syrup) crystallisation of the maltose or catalytic hydrogenation.

Hydrogenation of such a hydrolysate is carried out according to the rules of the art which lead, for example, to the production of sorbitol from glucose.

For this stage, catalysts based on ruthenium can be used just as well as RANEY nickel catalysts. However, the use of the RANEY nickel catalysts which are less expensive is preferred.

In practice, between 1 and 10% by weight of catalyst is used in relation to the dry matter of the hydrolysate subjected to hydrogenation. The hydrogenation is preferably carried out on a hydrolysate, the dry matter of which is between 15 and 50%, in practice close to 30 to 45%, under a hydrogen pressure of between 20 and 200 bar. It can be carried out continuously or discontinuously.

When the process is discontinuous, the hydrogen pressure used is generally between 30 and 60 bar and the temperature at which the hydrogenation takes place is between 100 and 150° C. Care is also taken to maintain the pH of the hydrogenation medium by the addition of soda or of sodium carbonate, for example, but without exceeding a pH of 9.0. This way of operating makes it possible to avoid any cracking or isomerisation products appearing.

The reaction is stopped when the content of reducing sugars in the reaction medium has become lower than 1%, by preference even lower than 0.5% and more particularly lower than 0.1%.

After cooling the reaction medium, the catalyst is eliminated by filtration and the maltitol syrup thus obtained is demineralised on cationic and anionic resins. At this stage, the syrups contain at least 93% maltitol.

The maltitol syrup obtained at the preceding hydrogenation stage can then undergo a stage of crystallisation so as to obtain crystallised maltitol.

According to a preferred embodiment of the method according to the invention, there is carried out on the maltitol syrup obtained in the preceding hydrogenation stage, the succession of stages consisting in:

concentrating the maltitol syrup;

crystallising and separating the maltitol crystals formed;

carrying out on the crystallisation mother liquids molecular sieving and, in particular, chromatographic fractionation so as to obtain a fraction which is enriched with maltitol and a fraction which is depleted in maltitol;

recycling the fraction which is enriched with maltitol, upstream of the crystallisation stage;

possibly carrying out on the fraction which is depleted in maltitol, either an acidic hydrolysis, and/or an enzymatic hydrolysis by means of, for example, an immobilised or non-immobilised amyloglucosidase;

possibly carrying out hydrogenation of said fraction which is depleted in maltitol and hydrolysed, in order to transform it into a sorbitol syrup.

Other characteristics and advantages of the invention will appear clearly in reading the following examples. They are, however, given here only by way of non-restrictive example.

EXAMPLE 1

Substrate: XAD761 resin marketed by the Company ROHM and HAAS.

Enzyme solution: Maltogénase® 4000 L, marketed by the company NOVO, diluted to half.

The solution is percolated in a closed circuit over a column filled with previously rehydrated resin, at a flow rate in the region of 3 to 4 bvh for one night, at ambient temperature. The balance of the activity is carried out by measuring the enzymatic activity of the solution (according to the method NOVO AF 203/1-GB) before and after percolation: 4445 units were fixed per ml of substrate, or the equivalent of 1 ml Maltogénase® 4000L.

EXAMPLE 2

Substrate: XAD 761 resin marketed by the company ROHM & HAAS.

Enzyme solution: Maltogénase® 4000L, marketed by the company NOVO, diluted to 9/20.

The solution is percolated in a closed circuit over a column filled with previously rehydrated resin, at a flow rate of 10 bvh/h, or 1000 l/h, at a temperature of 60° C., for 6 hours. The balance of the activity is carried out by measuring the enzymatic activity of the solution (according to the method NOVO AF 203/1-GB) before and after percolation: 4000 units were fixed per ml of substrate, or the equivalent of 1 ml of Maltogénase® 4000L, with a yield of 89% expressed in the number of units of fixed maltogenic α-amylase over the total number of units of maltogenic α-amylase introduced.

EXAMPLE 3

A starch milk, with 31% dry matter, is liquefied in standard fashion with the aid of 0.2% TERMAMYL® 120L (α-amylase marketed by the company NOVO) to a pH of 5.7 to 6.5 up to a DE slightly below 4.

Then the reaction medium is heated for a few seconds at 140° C. so as to inhibit the α-amylase, then the pH is adjusted between 5 and 5.5 and the temperature is adjusted to 55° C.

Saccharification is carried out to a dry matter of 25%, or slightly less, in the presence of pullulanase (PULLUZYME® 750L marketed by the company ABM) and of β-amylase (SPEZYME® BBA marketed by the company GENENCOR) at respective doses of 0.1% and 0.05% of the dry matter.

The saccharification, which lasts approximately 48 hours, gives a hydrolysate showing the following composition, DP1: 1.4%, DP2: 82.4%, DP3: 13.2%, DP4 and more: 2.6%.

The hydrolysate then undergoes standard purification by filtration, decoloration and demineralisation, then is concentrated to approximately 20% dry matter and adjusted to pH 5.5.

EXAMPLE 4

The hydrolysate of Example 3 is passed over a column filled with the enzyme obtained in Example 1 and thermostatted at 60° C. The composition of the maltose hydrolysate obtained depending on the flow rate is the following:

| Flow rate (bv/h) | DP1 | DP2 | DP3 | DP4 and + |
|---|---|---|---|---|
| 5 | 6.2 | 90.5 | 0.8 | 2.4 |
| 6 | 6.3 | 90.1 | 1 | 2.5 |

EXAMPLE 5

The next step is a stage of continuous chromatography of the maltose hydrolysate such as obtained in Example 3 above, in the following manner.

4 columns of a liter of sodic resin PCR 732 are assembled in series and supplied continuously with the maltose hydrolysate brought to a dry matter of 60% by weight, at a flow rate of 110 ml/h.

As they leave the column, the fractions enriched with maltose are recovered and have the following composition: DP1: 1.5%, DP2: 94%, DP3: 4.5%.

The chromatographic yield of maltose is 91.5%.

In the same manner as in Example 3, these fractions enriched with maltose are passed over a column filled with the enzyme obtained in Example 1 and thermostatted to 60° C. The composition of the maltose syrup obtained depending on the flow rate is the following:

| Flow rate (bv/h) | DP1 | DP2 | DP3 |
|---|---|---|---|
| 10 | 4 | 95.5 | 0.5 |

EXAMPLE 6

The maltose syrup obtained in Example 5 above is subjected to a stage of crystallisation of the maltose in the following manner. A maltose solution with a dry matter of 75% by weight is prepared at a temperature of 75° C. The maltose solution is sown with 5% by weight of germs of maltose crystals and the solution cooled from 75° C. to 40° C., at a rate of 0.5° C. per hour, stirring the solution at 50 rpm in a crystalliser with a double wall.

At the end of crystallisation, the crystals are separated from the mother liquid with the aid of a conventional centrifugal dryer.

The crystallisation yield is 50% by weight expressed in weight of crystallised maltose over the initial weight of maltose. The purity of maltose of the crystals recovered is 97.5% of the dry matter. The water content is 5%.

EXAMPLE 7

The maltose syrup coming from Example 5 is demineralised then hydrogenated in the following conditions:

| | |
|---|---|
| Dry matter | 40% |
| Temperature | 115° C. |
| Catalyst dose | 5% W/W dry |
| Pressure of $H_2$ | 50 bar |

The reaction is stopped when the reducing sugars are less than 0.3%. The medium is then filtered, demineralised and concentrated to 85% dry matter; its composition is:

| | |
|---|---|
| Sorbitol | 5.5% |
| Maltitol | 94.0% |
| Hydrogenated superiors | 0.5% |

The next step is the stage of crystallisation by cooling from 75 to 25° C., at a rate of 0.5° C./hour, with slow stirring, with priming of 6% P/P dry of crystallised maltitol with a grain size of between 200 and 250 μm.

After passing through a turbine, the crystals are dried and have a strength of 99.7%; the mother liquids are adjusted to 60% dry matter and subjected to chromatography.

Four columns of a liter of PCR732 resin, in calcium form, thermostatted to 85° C., are assembled in series and supplied continuously at a flow rate of 120 ml/h. The maltitol yield is 90.7% and the noble fraction (fraction rich in maltitol) has the following composition: sorbitol 4.5%; maltitol 95%; hydrogenated superiors: 0.5%.

The fraction depleted in maltitol, containing 53.5% sorbitol, 42.5% maltitol and 4% hydrogenated superiors, is then subjected to a stage of acidic hydrolysis.

The hydrolysis of the depleted fraction is realised continuously, on cation exchange resin, of the type C145 of Purolite, in the form H⁺ placed in a column thermostatted to 115° C.; by supplying the column at 1 bv/h with the solution concentrated to 40%, the following composition is obtained: sorbitol: 70.5%; maltitol: 12.3%; superiors: 0.4%; glucose: 16.8%.

This solution is then demineralised and hydrogenated in the following conditions:

Dry matter: 40%

Temperature: 135° C.

Catalyst dose: 5% P/Pdry

Hydrogen pressure: 50 bar, until a level of free reducing sugars lower than 0.1% is obtained.

What is claimed is:

1. A method of manufacturing a maltose-rich syrup, comprising the successive steps of:
   (a) carrying out liquefaction of a starch milk;
   (b) carrying out saccharification of the liquefied starch milk in the presence of a β-amylase, and at least one debranching enzyme selected from the group consisting of pullulanases and isoamylases;
   (c) bringing the liquefied and saccharified starch milk into contact with an immobilized maltogenic α-amylase which is adsorbed on particles of at least one porous substrate having an average pore diameter of between 200 and 800 Å and a particle diameter of between 0.2 and 1.2 mm in order to obtain a syrup which is rich in maltose.

2. A method according to claim 1, further comprising a step of crystallization of the syrup which is rich in maltose obtained in step (c), so as to obtain crystallized maltose.

3. A method according to claim 1, further comprising a step of hydrogenation of the syrup which is rich in maltose obtained in step (c), so as to obtain a maltitol-rich syrup.

4. A method according to claim 1, further comprising a step of hydrogenation of the syrup which is rich in maltose obtained in step (c), so as to obtain a maltitol-rich syrup and then crystallizing said maltitol-rich syrup in order to obtain a crystallized maltitol-rich syrup.

5. A method according to claim 1, further comprising a step of hydrogenation of the syrup which is rich in maltose obtained in step (c), so as to obtain a maltitol-rich syrup, said method comprising the additional steps of:
   (d) crystallizing the resulting maltitol-rich syrup in order to obtain a crystallized maltitol-rich syrup and mother liquors of crystallization;
   (e) performing a molecular sieving of the mother liquors of crystallization, so as to obtain a maltitol-enriched fraction and a maltitol-depleted fraction;
   (f) recycling the said maltitol-enriched fraction to the beginning of the crystallization stage;
   (g) performing acid and/or enzyme hydrolysis of said maltitol-depleted fraction;
   (h) performing hydrogenation of said maltitol-depleted and hydrolyzed fraction.

6. A method according to claim 1, wherein a molecular sieving step is performed on the syrup which is rich in maltose obtained in stage (c).

7. A method of manufacturing a maltose-rich syrup, comprising the steps of:
   (a) carrying out liquefaction of a starch milk;
   (b) carrying out saccharification of the liquefied starch milk in the presence of a β-amylase, and at least one debranching enzyme selected from the group consisting of pullulanases and isoamylases;
   (c) performing a molecular sieving of the liquefied and saccharified starch milk so as to obtain a maltose-enriched fraction and a maltose-depleted fraction;
   (d) bringing the said maltose-enriched fraction into contact with an immobilized maltogenic α-amylase which is adsorbed on particles of at least one porous substrate having an average pore diameter of between 200 and 800 Å and a particle diameter of between 0.2 and 1.2 mm in order to obtain a syrup which is rich in maltose.

8. A method according to claim 7, further comprising a step of crystallization of the syrup which is rich in maltose obtained in step (d), so as to obtain crystallized maltose.

9. A method according to claim 7 further comprising a step of hydrogenation of the syrup which is rich in maltose obtained in step (d), so as to obtain a maltitol-rich syrup.

10. A method according to claim 7 further comprising a step of hydrogenation of the syrup which is rich in maltose obtained in step (d), so as to obtain a maltitol-rich syrup and then crystallizing this maltitol-rich syrup in order to obtain a crystallized maltitol-rich syrup.

11. A method according to claim 7 further comprising a step of hydrogenation of the syrup which is rich in maltose obtained in step (d), so as to obtain a maltitol-rich syrup, said method comprising the additional steps of:
    (e) crystallizing the resulting maltitol-rich syrup in order to obtain a crystallized maltitol-rich syrup and mother liquors of crystallization;
    (f) performing a molecular sieving of the mother liquors of crystallization so as to obtain a maltitol-enriched fraction and a maltitol-depleted fraction;
    (g) recycling the said maltitol-enriched fraction before the crystallization stage;
    (h) performing acid and/or enzyme hydrolysis of said maltitol-depleted fraction;
    (i) performing a hydrogenation of said maltitol-depleted and hydrolyzed fraction.

\* \* \* \* \*